United States Patent
Xie et al.

(10) Patent No.: US 8,796,499 B2
(45) Date of Patent: Aug. 5, 2014

(54) PROCESS FOR PRODUCING LIGHT OLEFINS FROM METHANOL OR DIMETHYL ETHER

(75) Inventors: Zaiku Xie, Shanghai (CN); Juntao Liu, Shanghai (CN); Siqing Zhong, Shanghai (CN); Huiming Zhang, Shanghai (CN)

(73) Assignees: China Petroleum & Chemical Corporation, Beijing (CN); Shanghai Research Institute of Petrochemical Technology Sinopec, Shanghai (CN)

( * ) Notice: Subject to any disclaimer, the term of this patent is extended or adjusted under 35 U.S.C. 154(b) by 482 days.

(21) Appl. No.: 12/446,308

(22) PCT Filed: Oct. 19, 2007

(86) PCT No.: PCT/CN2007/002999
§ 371 (c)(1),
(2), (4) Date: Jun. 15, 2009

(87) PCT Pub. No.: WO2008/049328
PCT Pub. Date: May 2, 2008

(65) Prior Publication Data
US 2010/0063335 A1    Mar. 11, 2010

(30) Foreign Application Priority Data
Oct. 20, 2006   (CN) .......................... 2006 1 0117351

(51) Int. Cl.
*C07C 1/20* (2006.01)

(52) U.S. Cl.
USPC .......................................... 585/640; 585/639

(58) Field of Classification Search
USPC ......... 585/312, 638, 639, 640, 641, 901, 902, 585/903; 427/213; 422/131, 141, 142, 143, 422/144, 145, 146, 147, 613; 210/199, 209, 210/787, 803, 768; 502/21; 208/146, 176; 55/392, 392.1
See application file for complete search history.

(56) References Cited

U.S. PATENT DOCUMENTS

| | | | |
|---|---|---|---|
| 4,071,573 A * | 1/1978 | Owen et al. ................... | 585/402 |
| 4,748,052 A * | 5/1988 | Allen ............................. | 427/213 |
| 4,978,440 A * | 12/1990 | Krambeck et al. ............ | 208/113 |
| 6,166,282 A | 12/2000 | Miller | |
| 6,680,418 B2 | 1/2004 | Brown | |
| 2004/0064006 A1* | 4/2004 | Beech et al. .................. | 585/639 |
| 2006/0094915 A1* | 5/2006 | Palmas et al. ................ | 585/639 |

OTHER PUBLICATIONS

Canadian Office Action dated Mar. 6, 2012 issued in Application No. 2,666,852.

* cited by examiner

*Primary Examiner* — In Suk Bullock
*Assistant Examiner* — Candace R Chouinard
(74) *Attorney, Agent, or Firm* — Scully, Scott, Murphy & Presser, P.C.

(57) ABSTRACT

A process for producing light olefins from methanol and/or dimethyl ether is disclosed. It comprises: (a) introducing a feed comprising methanol and/or dimethyl ether into a fluidized-bed reactor from its bottom, and contacting the feed in a dense phase zone and a transition zone of the fluidized-bed reactor with a catalyst, to form an effluent I comprising unreacted feed, reaction products and entrained solid particulate catalyst; (b) introducing a terminating agent consisting of water, alcohol, ether, hydrocarbons, and aromatic at upper portion of the transition zone and/or lower portion of a gas-solid separating zone of the fluidized-bed reactor into the effluent I, to give an effluent II; and (c) passing the effluent II into the gas-solid separating zone in upper portion of the fluidized-bed reactor, where gas-solid separation is accomplished to give a gaseous product stream and solid catalyst.

9 Claims, 2 Drawing Sheets

US 8,796,499 B2

PROCESS FOR PRODUCING LIGHT OLEFINS FROM METHANOL OR DIMETHYL ETHER

CROSS REFERENCE OF RELATED APPLICATIONS

The present application claims the benefit of the Chinese Patent Application No. 200610117351.6, filed on Oct. 20, 2006, which is incorporated herein by reference in its entirety and for all purposes.

FIELD OF THE INVENTION

The present invention relates to a process for producing light olefins from methanol and/or dimethyl ether, in particular to a process for producing light olefins by highly efficient, catalytic conversion of methanol and/or dimethyl ether.

BACKGROUND OF THE INVENTION

Ethylene and propylene are important basic chemical feedstock. Ethylene is used mainly in the production of polyethylene, ethylene oxide, ethylene glycol, polyvinyl chloride, styrene, vinyl acetate, etc. Propylene is used mainly in the production of polypropylene, cumene, carbonyl alcohol, acrylonitrile, propylene oxide, acrylic acid, isopropanol, etc. At present, ethylene and propylene are mainly produced through catalytic cracking or steam cracking of petroleum feeds. However, other processes for producing ethylene and propylene are paid more and more regard as the petroleum resource is being depleted and the prices of petroleum have been rising.

It has been known for some time that oxygenates, especially alcohols, are convertible into light olefins. There are numerous technologies available for producing oxygenates. For example, syngas may be produced from coal or natural gas and further converted into methanol. Therefore, producing light olefins from oxygenates, especially methanol, is a promising approach.

Chinese Patent Application CN1166478A discloses a method for producing light olefins such as ethylene, propylene, and the like from methanol or dimethyl ether, which method utilizes an aluminum phosphate molecular sieve as catalyst, and uses a circularly fluidizing process using an upward flow dense phase bed. Under preferred conditions including a reaction temperature of from 500 to 570° C., a space velocity of from 2 to 6 $h^{-1}$, and a pressure of from 0.01 to 0.05 MPa, methanol or dimethyl ether is converted into light olefins, such as ethylene, propylene, and the like.

Chinese Patent Application CN1356299A discloses a process and a system for producing light olefins from methanol or dimethyl ether. This process utilizes a silicoaluminophosphate molecular sieve (SAPO-34) as catalyst, and uses a very shortly contacting fluidized bed reactor in which gas and solid co-flow downwardly. A feed contacts with the catalyst and reacts in the reactor, with the direction of the stream being downward; after exiting the reactor, the catalyst and reaction products enter gas-solid quickly separating unit located below the reactor to be quickly separated from each other; the separated catalyst is then passed into a regenerator to be regenerated by burning off carbon. This process achieves conversions of dimethyl ether or methanol of larger than 98%.

However, there is still need for a process for producing light olefins from methanol and/or dimethyl ether, which process achieves higher yield of and better selectivity to ethylene and propylene.

SUMMARY OF THE INVENTION

An object of the invention is to provide a process for producing light olefins from methanol and/or dimethyl ether comprising the steps of:

(a) introducing a feed comprising methanol and/or dimethyl ether into a fluidized-bed reactor from its bottom, and reacting the feed in a dense phase zone and a transition zone of the fluidized-bed reactor by contacting it with a catalyst, to form an effluent I comprising unreacted feed, reaction products and entrained solid particulate catalyst;

(b) introducing a terminating agent at upper portion of the transition zone and/or lower portion of a gas-solid separating zone of the fluidized-bed reactor into the effluent I, to give an effluent II, wherein the terminating agent is at least one selected from the group consisting of water, $C_2$ to $C_5$ alcohols, $C_2$ to $C_{10}$ ethers, hydrocarbons having 4 or more carbon atoms, and $C_6$ to $C_{12}$ aromatic hydrocarbons; and (c) passing the effluent II into the gas-solid separating zone in upper portion of the fluidized-bed reactor, where gas-solid separation is accomplished to give a gaseous product stream and solid catalyst, said gaseous product stream being led to an after-treatment stage, and said solid catalyst being circulated to the dense phase zone in lower portion of the fluidized-bed reactor or, alternatively, being led to a regenerator after having been stripped in a stripper.

In a preferred embodiment, the effluent II passed into the gas-solid separating zone is first passed through a whirl-flow quickly-separating unit to separate out most of the entrained solid catalyst particles, and the resultant gaseous stream III containing the remaining entrained catalyst particles is leaded into a cyclone and is separated there into a particulate catalyst stream and the gaseous product stream. In a preferred aspect of this preferred embodiment, the cyclone is an outside-type cyclone, that is to say, the cyclone is located outside the settling section of the gas-solid separating zone of the reactor.

DETAILED DESCRIPTION THE PREFERRED EMBODIMENTS

Figure 1:
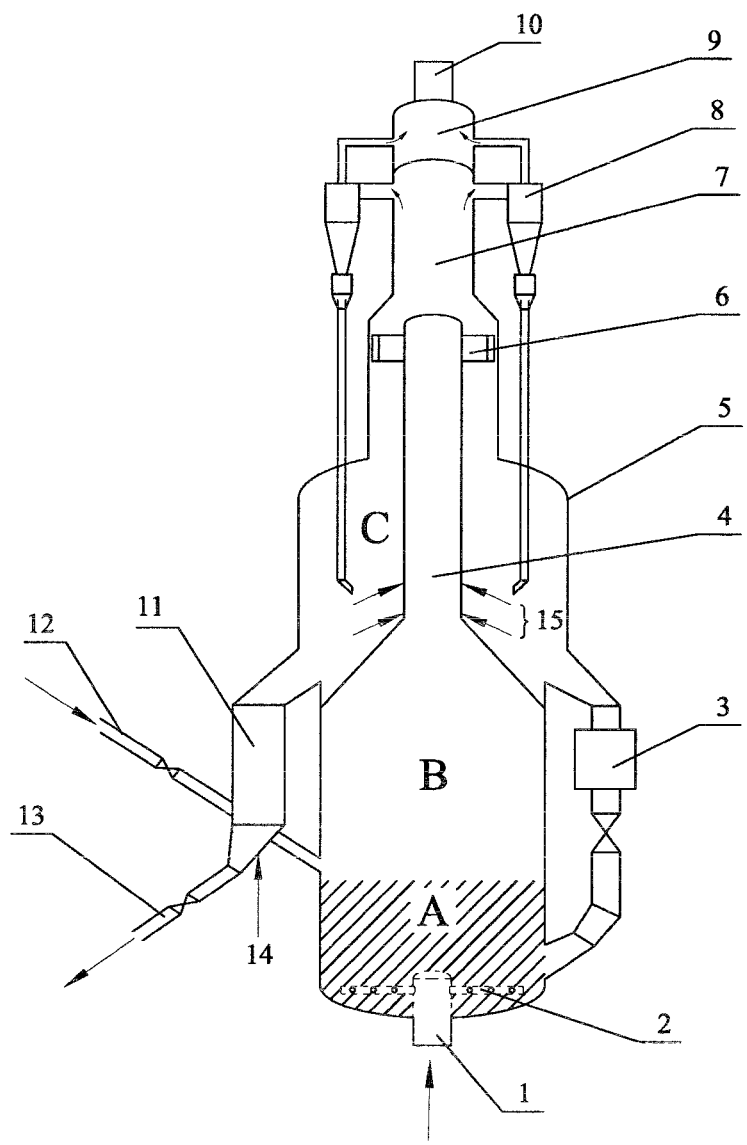
FIG. 1 is a schematic diagram of a fluidized-bed reactor useful in the process according to the invention.

As used herein, the term "light olefin" means ethylene, propylene, butane, and mixtures thereof, especially ethylene, propylene, and mixtures thereof.

The process for producing light olefins from methanol and/or dimethyl ether according to the invention utilizes a fluidized-bed reactor. The fluidized-bed reactor may be selected from the group consisting of bubbling fluidized bed reactors, turbulent fluidized bed reactors, fast fluidized bed reactors and riser reactor. The fluidized-bed reactor is preferably a fast fluidized bed reactor.

In general, the inner volume of a fluidized-bed reactor can be divided into a dense phase zone, a transition zone, and a gas-solid separating zone, depending on reaction status in and function of the zones. The dense phase zone means a reactor section in which a large amount of the catalyst used is contained and most of the conversion reaction of the feed to olefins is accomplished. The gas-solid separating zone means a reactor section that is designed to accomplish the separation of the gaseous stream from the solid catalyst entrained. However, in the gas-solid separating zone, it is usual that some reactions still take place due to that the reaction mixture is still at higher temperature and due to the presence of the catalyst. The transition zone means a reactor section between the dense phase zone and the gas-solid separating zone.

In the process according to the invention, the feed comprising methanol and/or dimethyl ether is introduced into the fluidized-bed reactor at its bottom, and reacts in the dense phase zone and the transition zone of the fluidized-bed reactor by contacting with the catalyst, to form an effluent I comprising unreacted feed, reaction products and entrained solid catalyst. The reaction products include ethylene, propylene, hydrocarbons having 4 or more carbon atoms.

In an embodiment, the feed contains further one or more diluent(s). The diluents are typically used to reduce the concentration of methanol and/or dimethyl ether, and are generally non-reactive to methanol and/or dimethyl ether as well as the used catalyst. Non-limiting examples of the diluent include water, nitrogen, carbon monoxide, carbon dioxide, methane, ethane, propane, and argon, among these water and nitrogen are preferable.

Reaction conditions include: a reaction temperature, defined herein as the temperature in the dense phase zone, in a range of from 200 to 600° C., and preferably from 300 to 550° C.; a reaction pressure in a range of from 0.01 to 1.5 MPa, and preferably from 0.05 to 1.0 MPa; a contacting time, also referred to as residence time of the feed in the reactor, in a range of from 0.1 to 20 s, and preferably from 0.2 to 10 s; and a weight ratio of the catalyst to the feed, also referred to as catalyst/oil ratio and meaning a ratio of the total weight of regenerated catalyst and optional fresh catalyst added into the reactor in a unit of time to the total weight of methanol and/or dimethyl ether in the feed to the reactor in the same time, of from 0.1 to 50, and preferably from 0.2 to 10.

Those catalysts known in the art suitable for the conversion reaction of methanol and/or dimethyl ether to olefins can be used in the process according to the invention. Preferably, the catalyst used in the present process is selected from the group consisting of silicoaluminophosphate molecular sieves, ZSM molecular sieves and combinations thereof. More preferably, the catalyst is selected from the group consisting of SAPO-34 molecular sieve, SAPO-11 molecular sieve, ZSM-5 molecular sieve, ZSM-35 molecular sieve and combinations thereof.

During the production of light olefins, especially ethylene and propylene, from methanol and/or dimethyl ether through catalytic conversion reaction using a fluidized-bed reactor, the target products, i.e., ethylene and propylene, are intermediate products of the reaction, and they may undergo further conversion reaction when contacting with the catalyst at a higher temperature for a long time. In methanol-to-olefin (MTO) processes known in the art using a fluidized-bed reactor, a settling section in the gas-solid separating zone of the fluidized-bed reactor accommodates typically a large amount of catalyst at a higher temperature. The desired reaction products will partially undergo further reaction under the action of the catalyst, resulting in low selectivity and low yield of ethylene and propylene. The present inventors have found that, by introducing a terminating agent into upper portion of the transition zone and/or lower portion of the gas-solid separating zone of the fluidized-bed reactor, the yield of the desired products (i.e., ethylene and propylene) can be effectively enhanced. Non-limiting examples of terminating agent useful in the present process include water, $C_2$ to $C_5$ alcohol, $C_2$ to $C_{10}$ ethers, hydrocarbons having 4 or more carbon atoms, and $C_6$ to $C_{12}$ aromatic hydrocarbons.

Without limited to a specific theory, it is believed that the introduction of the terminating agent lowers effectively the temperature of the reaction mixture exiting the transition zone, thereby reducing the occurrence of side reactions. The terminating agent can be used in an amount of from ⅕ to 1/1000 of the total weight of the methanol and/or dimethyl ether as the starting material. When entering the reactor, the terminating agent can have a temperature of from 10 to 200° C., preferably from 15 to 150° C., and more preferably from 20 to 100° C.

In a preferred embodiment, the terminating agent can be conveniently introduced into the reactor at lower portion of the gas-solid separating zone.

After the introduction of the terminating agent, the reaction effluent II is separated in the gas-solid separating zone of the fluidized-bed reactor into a gaseous product stream, which comprises unreacted feed, reaction products and the terminating agent, and solid catalyst. The gaseous product stream is led to an after-treatment stage, to isolate ethylene and/or propylene as products. The method and conditions for after-treating the gaseous product stream are well known by those skilled in the art. The solid catalyst is circulated to the dense phase zone in the lower portion of the fluidized-bed reactor or, alternatively, passed into a regenerator to be regenerated after having been stripped in a stripper. The method and conditions for stripping and regenerating the solid catalyst are also well known by those skilled in the art.

In a preferred embodiment, the effluent II passed into the gas-solid separating zone is first passed through a whirl-flow quickly-separating unit to separate out most of the entrained solid catalyst particles, and the resultant gaseous stream III containing the remaining entrained catalyst particles is led into a cyclone and is separated there into a particulate catalyst stream and the gaseous product stream. In a preferred aspect of this preferred embodiment, the cyclone is an outside-type cyclone, that is to say, the cyclone is located outside the settling section of the gas-solid separating zone of the reactor. By using an outside-type cyclone, the volume of the settling section can be greatly reduced so that back-mixing of the mixed product gases in the settling section is reduced and residence time is shortened, and thus the secondary reactions are reduced. This is in favor of the enhancement of the yield of ethylene and propylene.

FIG. 1 depicts schematically a fluidized-bed reactor useful in the practice of the process according to the invention, wherein A represents a dense phase zone, B represents a transition zone, C represents a gas-solid separating zone, 1 is a feed inlet, 2 is a distributor or a distributing plate, 3 is a heat-exchanger, 4 is a riser, 5 is a settling section, 6 is a whirl-flow quickly-separating unit, 7 is a gas conduit, 8 is a cyclone, 9 is a gas collection chamber, 10 is a gaseous product stream outlet, 11 is a stripper, 12 is a regenerated catalyst feeding line, 13 is a catalyst discharging line connected to a regenerator, 14 is a stripping steam inlet, and 15 is a terminating agent inlet.

Figure 2:
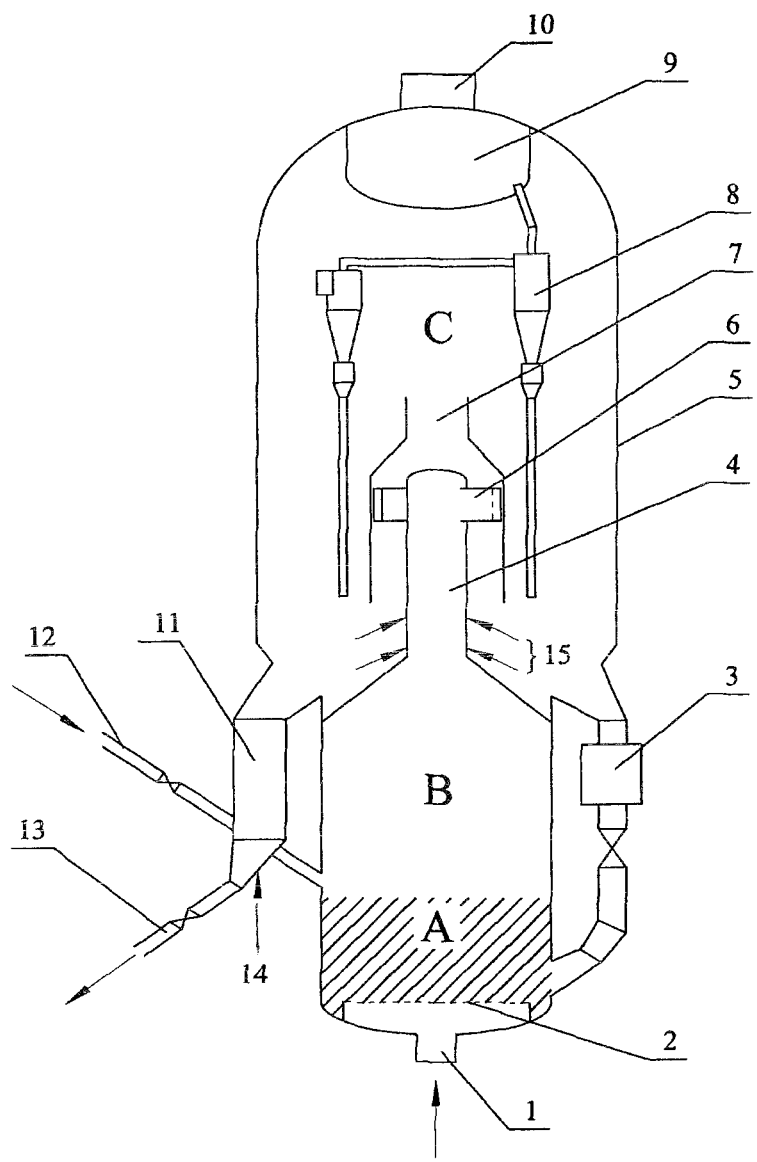
FIG. 2 depicts a fluidized-bed reactor used in the comparative examples.

FIG. 2 depicts a fluidized-bed reactor used in the comparative examples below, wherein the individual symbols have the same meanings as given for FIG. 1.

By reference to the FIG. 1, a feed is introduced from the feed inlet 1 into the dense phase zone A of the fluidized-bed reactor through the distributor or distributing plate 2, and reacts by contacting with a catalyst. An effluent entraining solid catalyst particles passes through the transition zone B and then enters the riser 4. A terminating agent is introduced into the effluent at the lower portion of the riser 4 via the terminating agent inlet 15. After the effluent is quickly separated in the whirl-flow quickly-separating unit 6 located at upper end of the riser 4, most of the entrained catalyst enters lower portion of the settling section 5, and a reaction effluent still entraining some catalyst particles enters the cyclone 8 via the gas conduit 7 to be further separated. A gaseous stream from the cyclone 8 enters the gas collection chamber 9 via an outlet of the cyclone 8, and then is withdrawn via the gaseous product stream outlet 10. Solid particulate catalyst from the cyclone 8 is led to the lower portion of the settling section 5 via a discharging leg of the cyclone 8. A portion of the catalyst in the lower portion of the settling section 5 is led to the stripper 11 and stripped with a steam introduced via the stripping steam inlet 14, and then led to a regenerator (not shown) via the catalyst discharging line 13. Regenerated catalyst is recycled to the dense phase zone A of the fluidized-bed reactor via the catalyst feeding line 12. In addition, a portion of the catalyst in the settling section 5 is led to the lower portion of the dense phase zone A of the fluidized-bed reactor after having been subjected to heat-exchanging in the heat-exchanger 3.

The process according to the invention enhances the yield of ethylene and propylene.

EXAMPLES

The following examples are given for further illustrating the invention, but do not make limitation to the invention in any way.

Example 1

An experiment was conducted in a unit as shown in FIG. 1, wherein SAPO-34 was used as a catalyst, methanol was used as a feed, ethanol was used as a terminating agent, the weight ratio of the feed to the terminating agent was 20:1, and the feeding temperature of the terminating agent was 23° C. The reaction conditions in the fluidized-bed reactor were as follows: reaction temperature=470° C. reaction pressure=0.05 MPa, contacting time=7 s, weight ratio of the catalyst to methanol=1. The reaction results are as follows: yield of ethylene=48.4%, and yield of propylene=34.2%.

Example 2

An experiment was conducted in the unit as shown in FIG. 1, wherein SAPO-34 was used as a catalyst, methanol was used as a feed, water was used as a terminating agent, the weight ratio of the feed to the terminating agent was 10:1, and the feeding temperature of the terminating agent was 60° C. The reaction conditions in the fluidized-bed reactor were as follows: reaction temperature=450° C., reaction pressure=0.01 MPa, contacting time=3 s, weight ratio of the catalyst to methanol=0.7. The reaction results are as follows: yield of ethylene=44.7%, and yield of propylene=29.1%.

Example 3

An experiment was conducted in the unit as shown in FIG. 1, wherein SAPO-34 was used as a catalyst, dimethyl ether was used as a feed, methyl tert-butyl ether was used as a terminating agent, the weight ratio of the feed to the terminating agent was 35:1, and the feeding temperature of the terminating agent was 23° C. The reaction conditions in the fluidized-bed reactor were as follows: reaction temperature=570° C., reaction pressure=0.8 MPa, contacting time=10 s, weight ratio of the catalyst to dimethyl ether=1.2. The reaction results are as follows: yield of ethylene=49.3%, and yield of propylene=30.8%.

Example 4

An experiment was conducted in the unit as shown in FIG. 1, wherein SAPO-34 was used as a catalyst, dimethyl ether was used as a feed, ethyl tert-butyl ether was used as a terminating agent, the weight ratio of the feed to the terminating agent was 50:1, and the feeding temperature of the terminating agent was 23° C. The reaction conditions in the fluidized-bed reactor were as follows: reaction temperature=520° C., reaction pressure=1.2 MPa, contacting time=15 s, weight ratio of the catalyst to dimethyl ether=7. The reaction results are as follows: yield of ethylene=42.6%, and yield of propylene=30.8%.

Example 5

An experiment was conducted in the unit as shown in FIG. 1, wherein SAPO-34 was used as a catalyst, a mixture of methanol and dimethyl ether in 1:1 weight ratio was used as a feed, propanol was used as a terminating agent, the weight ratio of the feed to the terminating agent was 100:1, and the feeding temperature of the terminating agent was 23° C. The reaction conditions in the fluidized-bed reactor were as follows: reaction temperature=550° C., reaction pressure=0.2 MPa, contacting time=5 s, weight ratio of the catalyst to the feed=0.5. The reaction results are as follows: yield of ethylene=45.7%, and yield of propylene=39.9%.

Example 6

An experiment was conducted in the unit as shown in FIG. 1, wherein a mixed molecular sieve catalyst comprising 2 wt % of ZSM-5, 88 wt % of SAPO-34, and 10 wt % of silica as binder was used, a mixture of methanol and dimethyl ether in 2:1 weight ratio was used as a feed, water was used as a terminating agent, the weight ratio of the feed to the terminating agent was 30:1, and the feeding temperature of the terminating agent was 50° C. The reaction conditions in the fluidized-bed reactor were as follows: reaction temperature=500° C., reaction pressure=0.2 MPa, contacting time=8 s, weight ratio of the catalyst to the feed=1. The reaction results are as follows: yield of ethylene=34.1%, and yield of propylene=46.1%.

Example 7

An experiment was conducted in the unit as shown in FIG. 1, wherein a mixed molecular sieve catalyst comprising 5 wt % of ZSM-5, 80 wt % of SAPO-34, and 15 wt % of silica as binder was used, a mixture of methanol and dimethyl ether in 5:1 weight ratio was used as a feed, ethanol was used as a terminating agent, the weight ratio of the feed to the terminating agent was 50:1, and the feeding temperature of the terminating agent was 40° C. The reaction conditions in the fluidized-bed reactor were as follows: reaction temperature=510° C., reaction pressure=0.4 MPa, contacting time=5 s, weight ratio of the catalyst to the feed=0.8. The reaction results are as follows: yield of ethylene=44.7%, and yield of propylene=36.8%.

Example 8

An experiment was conducted in the unit as shown in FIG. 1, wherein SAPO-11 was used as a catalyst, methanol was used as a feed, water was used as a terminating agent, the weight ratio of the feed to the terminating agent was 6:1, and the feeding temperature of the terminating agent was 30° C. The reaction conditions were as follows: reaction temperature=510° C., reaction pressure=0.1 MPa, contacting time=3 s, weight ratio of the catalyst to the feed=0.5. The reaction results are as follows: yield of ethylene=23.8%, and yield of propylene=45.2%.

Example 9

An experiment was conducted in the unit as shown in FIG. 1, wherein ZSM-35 was used as a catalyst, methanol was used as a feed, ethanol was used as a terminating agent, the weight ratio of the feed to the terminating agent was 10:1, and the feeding temperature of the terminating agent was 80° C. The reaction conditions in the fluidized-bed reactor were as follows: reaction temperature=510° C., reaction pressure=0.1 MPa, contacting time=3 s, weight ratio of the catalyst to the feed=0.5. The reaction results are as follows: yield of ethylene=14.7%, and yield of propylene=42.4%.

Comparative Example 1

An experiment was conducted in a unit, in which the cyclone was an inside-type cyclone, as shown in FIG. 2. The catalyst and reaction conditions employed were the same as described in Example 1. The reaction results are as follows: yield of ethylene=43.4%, and yield of propylene=29.2%.

Comparative Example 2

An experiment was conducted in the unit, in which the cyclone was an inside-type cyclone, as shown in FIG. 2. The catalyst and reaction conditions employed were the same as described in Example 8. The reaction results are as follows: yield of ethylene=21.3%, and yield of propylene=41.1%.

Comparative Example 3

An experiment was conducted in the unit as shown in FIG. 1. The catalyst and reaction conditions employed were the same as described in Example 2, except for that no terminating agent was used. The reaction results are as follows: yield of ethylene=41.2% and yield of propylene=26.9%.

Comparative Example 4

An experiment was conducted in the unit as shown in FIG. 1. The catalyst and reaction conditions employed were the same as described in Example 3, except for that no terminating agent was used. The reaction results are as follows: yield of ethylene=46.5%, and yield of propylene=27.6%.

While the invention has been described with reference to exemplary embodiments, it will be understood by those skilled in the art that various changes and modifications may be made without departing from the spirit and scope of the invention. Therefore, the invention is not limited to the particular embodiments disclosed as the best mode contemplated for carrying out this invention, but the invention will include all embodiments falling within the scope of the appended claims.

What is claimed is:

1. A process for producing light olefins from methanol and/or dimethyl ether comprising the steps of:
    (a) introducing a feed comprising methanol and/or dimethyl ether into a fluidized-bed reactor from its bottom, and reacting the feed in a dense phase zone and a transition zone of the fluidized-bed reactor by contacting it with a catalyst, to form an effluent I comprising unreacted feed, reaction products and entrained solid particulate catalyst;
    (b) introducing a terminating agent at a lower portion of a gas-solid separating zone of the fluidized-bed reactor into the effluent I, to give an effluent II, wherein the terminating agent is at least one selected from the group consisting of water, $C_2$ to $C_5$ alcohols, $C_2$ to $C_{10}$ ethers, hydrocarbons having 4 or more carbon atoms, and $C_6$ to $C_{12}$ aromatic hydrocarbons; and
    (c) passing the effluent II into the gas-solid separating zone in upper portion of the fluidized-bed reactor, where gas-solid separation is accomplished to give a gaseous product stream and solid catalyst, said gaseous product stream being led to an after-treatment stage, and said solid catalyst being circulated to the dense phase zone in lower portion of the fluidized-bed reactor or, alternatively, being led to a regenerator after having been stripped in a stripper wherein the effluent II passed into the gas-solid separating zone is first passed through a whirl-flow quickly-separating unit to separate out most of the entrained solid particulate catalyst, and a resultant gaseous stream III containing the remaining entrained particulate catalyst is led into a outside-type cyclone and is separated there into a particulate catalyst stream and the gaseous product stream.

2. The process of claim 1, wherein the terminating agent is used in an amount of from 1/5 to 1/1000 of the total weight of methanol and/or dimethyl ether as the starting material, and when entering the reactor, has a temperature in the range of from 10 to 200° C.

3. The process of claim 1, wherein reaction conditions include: a reaction temperature of from 200 to 600° C., a reaction pressure of from 0.01 to 1.5 MPa, a contacting time of from 0.1 to 20 s, and a weight ratio of the catalyst to the feed of from 0.1 to 50.

4. The process of claim 3, wherein the reaction conditions include: a reaction temperature of from 300 to 550° C., a reaction pressure of from 0.05 to 1.0 MPa, a contacting time of from 0.2 to 10 s, and a weight ratio of the catalyst to the feed of from 0.2 to 10.

5. The process of claim 1, wherein the catalyst is selected from the group consisting of silicoaluminophosphate molecular sieves, ZSM molecular sieves, and combinations thereof.

6. The process of claim 5, wherein the catalyst is selected from the group consisting of SAPO-11 molecular sieve, SAPO-34 molecular sieve, ZSM-5 molecular sieve, ZSM-35 molecular sieve, and combinations thereof.

7. The process of claim 1, wherein the fluidized-bed reactor is selected from the group consisting of bubbling fluidized bed reactors, turbulent fluidized bed reactors, fast fluidized bed reactors and riser reactors.

8. The process of claim 7, wherein the fluidized-bed reactor is a fast fluidized bed reactor.

9. The process of claim 1, further comprising recycling a regenerated catalyst from the regenerator to the dense phase zone in lower portion of the fluidized-bed reactor.

* * * * *